(12) United States Patent
Hidaka et al.

(10) Patent No.: US 11,246,500 B2
(45) Date of Patent: Feb. 15, 2022

(54) BIOLOGICAL INFORMATION MEASUREMENT DEVICE, BIOLOGICAL INFORMATION MEASUREMENT SYSTEM, AND BIOLOGICAL INFORMATION MEASUREMENT METHOD

(71) Applicant: KYOCERA Corporation, Kyoto (JP)

(72) Inventors: Mizuho Hidaka, Yokohama (JP); Norikazu Morioka, Tama (JP)

(73) Assignee: KYOCERA Corporation, Kyoto (JP)

( * ) Notice: Subject to any disclaimer, the term of this patent is extended or adjusted under 35 U.S.C. 154(b) by 264 days.

(21) Appl. No.: 16/325,501

(22) PCT Filed: Aug. 2, 2017

(86) PCT No.: PCT/JP2017/028131
§ 371 (c)(1),
(2) Date: Feb. 14, 2019

(87) PCT Pub. No.: WO2018/043018
PCT Pub. Date: Mar. 8, 2018

(65) Prior Publication Data
US 2019/0167123 A1 Jun. 6, 2019

(30) Foreign Application Priority Data
Aug. 30, 2016 (JP) .............................. JP2016-168351

(51) Int. Cl.
*A61B 5/0245* (2006.01)
*A61B 5/1455* (2006.01)
(Continued)

(52) U.S. Cl.
CPC ............ *A61B 5/0245* (2013.01); *A61B 5/026* (2013.01); *A61B 5/0261* (2013.01);
(Continued)

(58) Field of Classification Search
CPC . A61B 5/024; A61B 5/02416; A61B 5/02427; A61B 5/02433; A61B 5/02444; A61B 5/0245; A61B 5/026–0261; A61B 5/0285–029; A61B 5/6803; A61B 5/6814–6816
See application file for complete search history.

(56) References Cited

U.S. PATENT DOCUMENTS 6,361,501 B1 * 3/2002 Amano ............... A61B 5/02028
600/485
6,783,501 B2 8/2004 Takahashi et al.
(Continued)

FOREIGN PATENT DOCUMENTS

JP  H02-32802 U   3/1990
JP  2001-245860 A  9/2001
(Continued)

*Primary Examiner* — Thaddeus B Cox
(74) *Attorney, Agent, or Firm* — Studebaker & Brackett PC

(57) ABSTRACT

A biological information measurement device comprising a sensor configured to measure biological information, wherein the sensor is supported by a wearing portion configured to be worn on a head of a human body, and is located at a position opposing at least any of an artery and a vein in the head when in a state in which the wearing portion is worn on the head.

14 Claims, 15 Drawing Sheets

(51) Int. Cl.
*A61B 5/021* (2006.01)
*A61B 5/11* (2006.01)
*A61B 5/026* (2006.01)
*A61B 5/024* (2006.01)
*A61B 5/00* (2006.01)

(52) U.S. Cl.
CPC ............ *A61B 5/02125* (2013.01); *A61B 5/11* (2013.01); *A61B 5/1455* (2013.01); *A61B 5/6803* (2013.01); *A61B 5/6816* (2013.01); *A61B 5/02438* (2013.01); *A61B 2560/0443* (2013.01)

(56) References Cited

U.S. PATENT DOCUMENTS

| | | | |
|---|---|---|---|
| 2003/0018274 A1 | 1/2003 | Takahashi et al. | |
| 2003/0163051 A1* | 8/2003 | Eckerle | A61B 5/6822 600/485 |
| 2010/0217099 A1* | 8/2010 | LeBoeuf | A61B 5/4812 600/301 |
| 2012/0029367 A1* | 2/2012 | Hobeika | A61B 5/02416 600/500 |
| 2012/0203077 A1* | 8/2012 | He | A61B 5/6815 600/301 |
| 2015/0250418 A1* | 9/2015 | Ashby | A61B 5/02433 600/474 |
| 2015/0342481 A1* | 12/2015 | Liu | A61B 5/721 600/479 |
| 2015/0366518 A1* | 12/2015 | Sampson | A61B 5/0261 600/301 |
| 2016/0089086 A1* | 3/2016 | Lin | A61B 5/721 600/479 |
| 2016/0324478 A1* | 11/2016 | Goldstein | A61B 5/721 |
| 2017/0343808 A1* | 11/2017 | Asayama | A61B 5/25 |
| 2018/0000413 A1 | 1/2018 | Masuda et al. | |
| 2018/0014741 A1* | 1/2018 | Chou | A61B 5/25 |
| 2018/0020979 A1* | 1/2018 | Wagner | A61B 5/0013 600/379 |
| 2018/0146866 A1* | 5/2018 | Chachisvilis | A61B 5/0261 |
| 2018/0214041 A1 | 8/2018 | Hidaka et al. | |
| 2018/0299922 A1* | 10/2018 | Park | A61B 5/7475 |

FOREIGN PATENT DOCUMENTS

| | | |
|---|---|---|
| JP | 2003-033328 A | 2/2003 |
| JP | 2015-223437 A | 12/2015 |
| JP | 2016-054840 A | 4/2016 |
| WO | 2009/001449 A1 | 12/2008 |
| WO | 2016/121399 A1 | 8/2016 |

* cited by examiner

FIG. 4

| PART NAME | MEASURED VALUE | | |
|---|---|---|---|
| | MINIMUM VALUE | MAXIMUM VALUE | DIFFERENCE VALUE |
| EYELID | — | — | — |
| NOSE | — | — | — |
| CHEEK | — | — | — |
| TRAGUS | 2415 | 2419 | 4 |
| EARLOBE | 1863 | 1869 | 6 |
| EAR CONCHA | 2159 | 2165 | 6 |
| FOREHEAD | 2185 | 2193 | 8 |
| LIPS | 1649 | 1657 | 8 |
| TEMPLE | 2125 | 2133 | 8 |
| AURICLE REAR | 2439 | 2447 | 8 |
| ANTITRAGUS | 2377 | 2385 | 8 |
| MASTOID PORTION | 1837 | 1845 | 8 |
| FLOATING WHITE | 1953 | 1963 | 10 |
| HARMONY CREVICE | 2193 | 2205 | 12 |

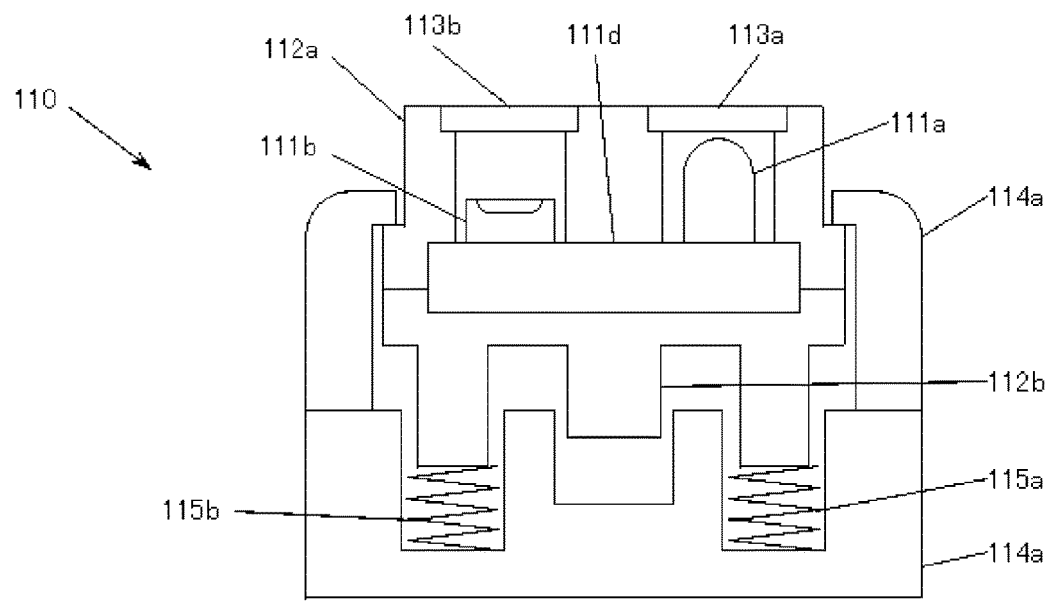
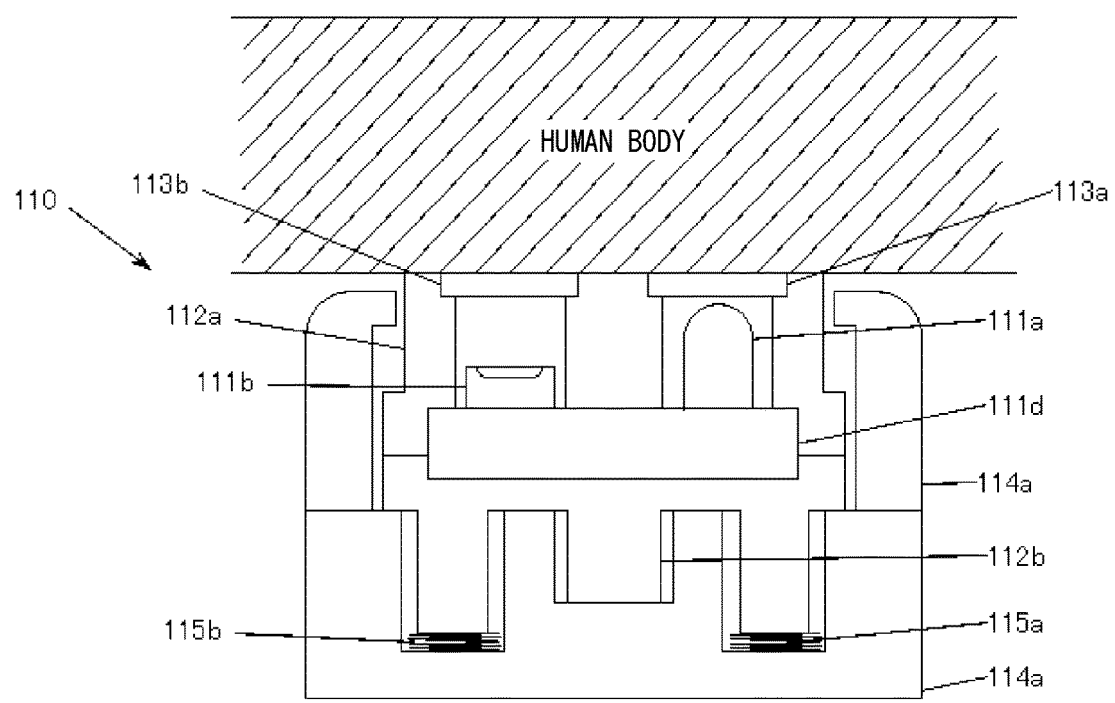
FIG. 11

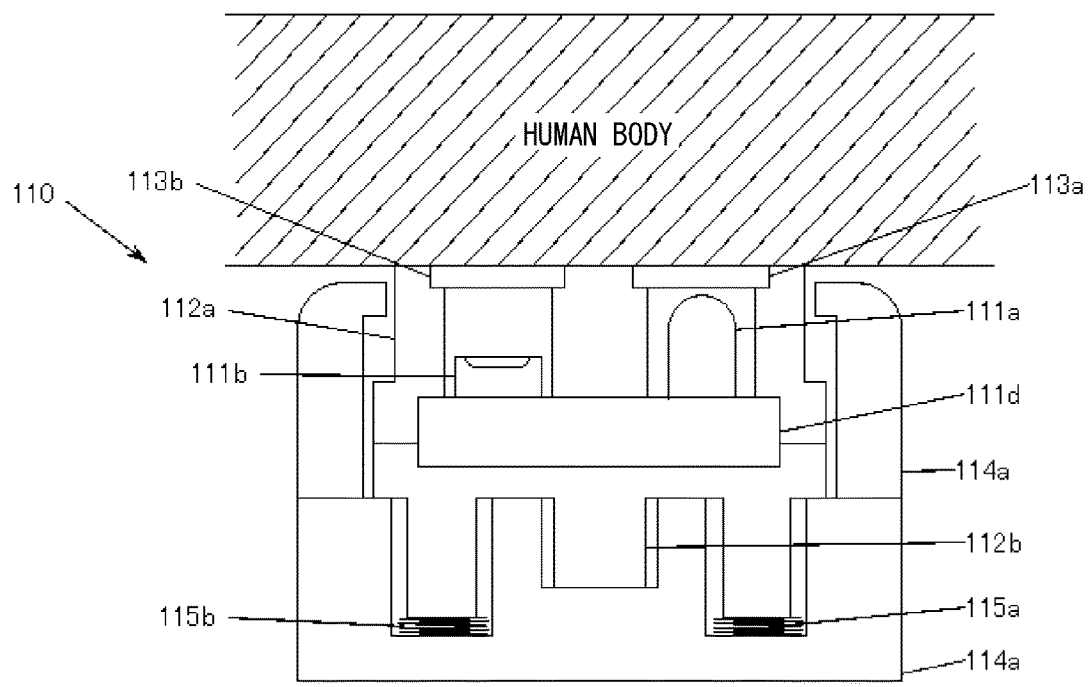
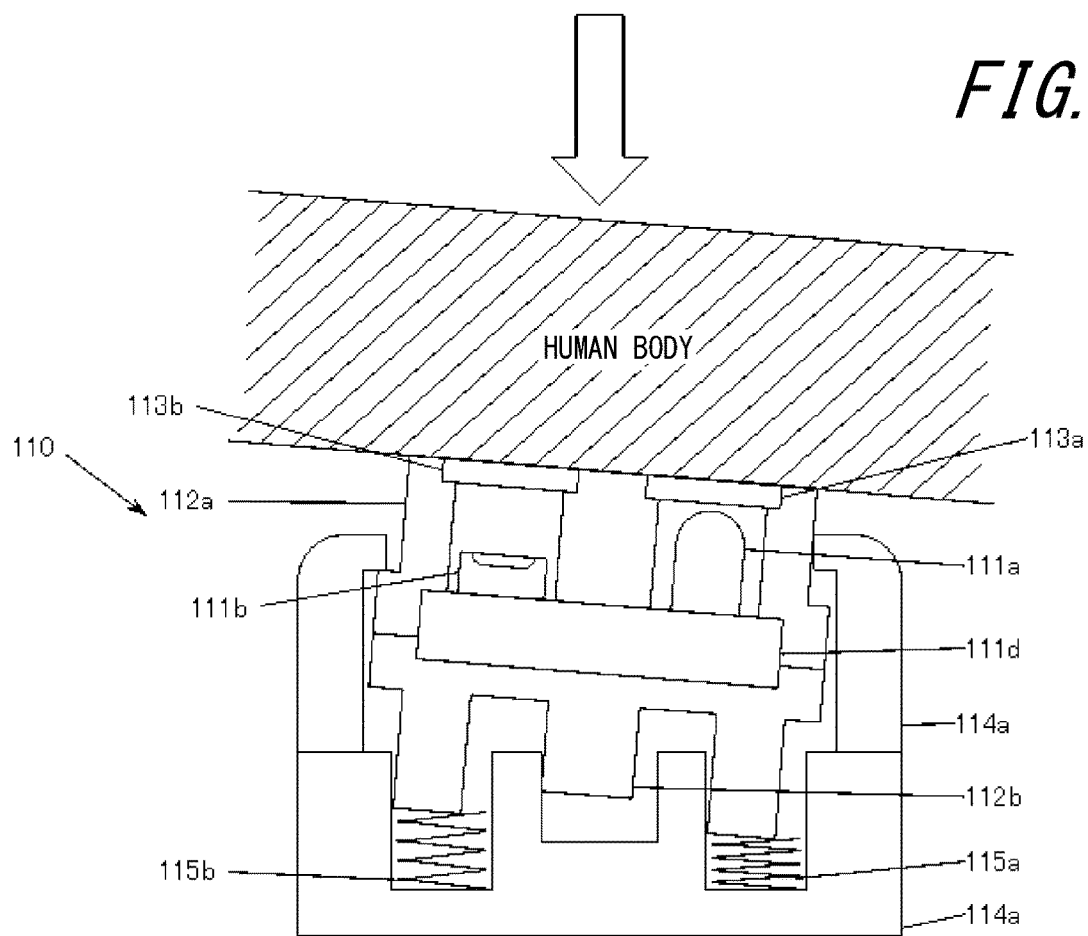
FIG. 12

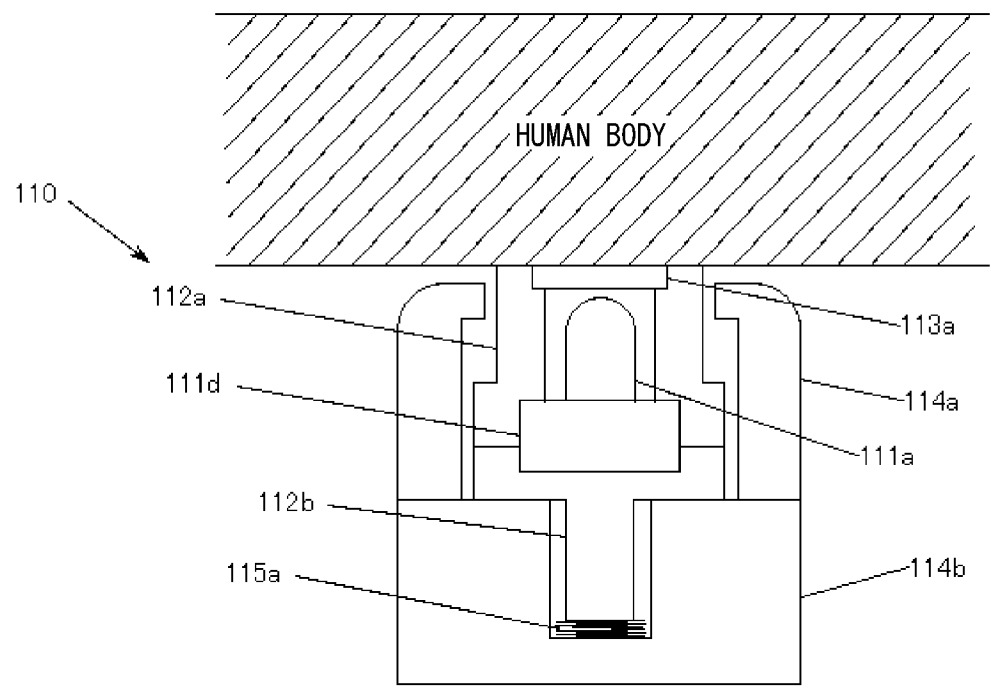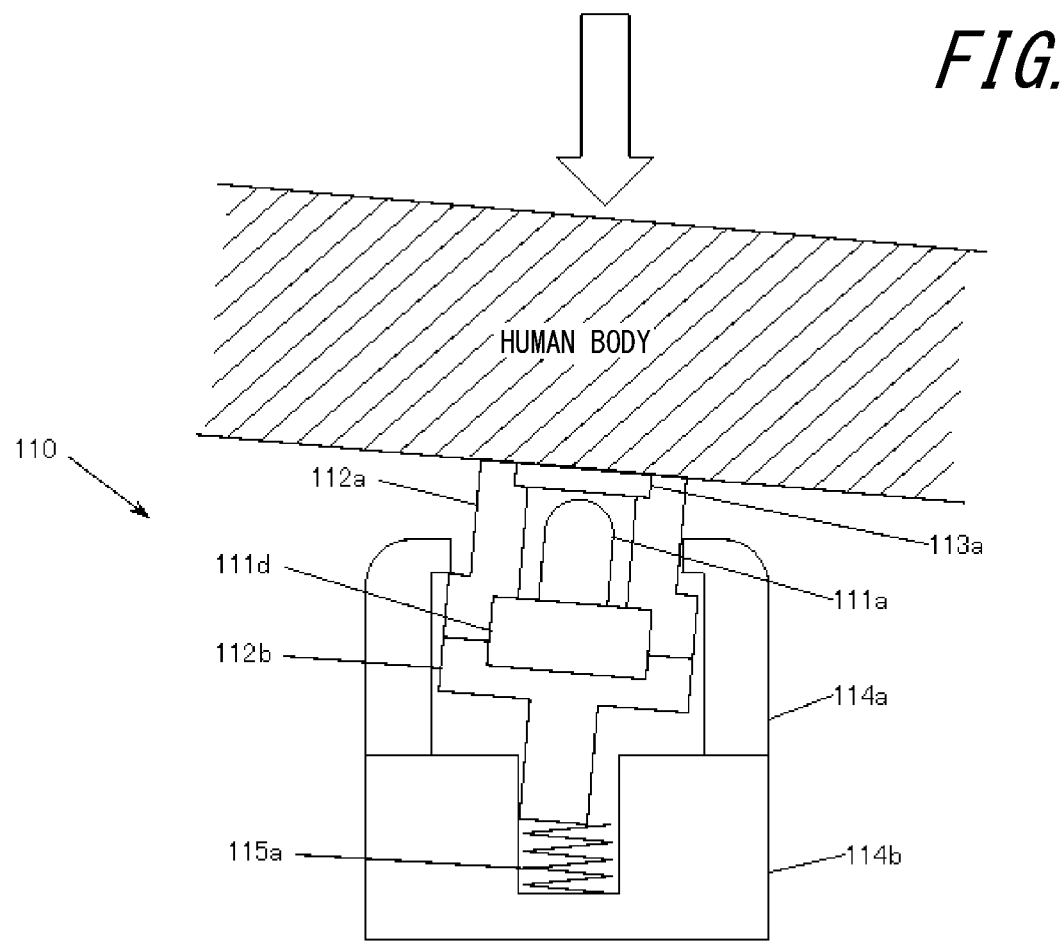
FIG. 13

US 11,246,500 B2

BIOLOGICAL INFORMATION MEASUREMENT DEVICE, BIOLOGICAL INFORMATION MEASUREMENT SYSTEM, AND BIOLOGICAL INFORMATION MEASUREMENT METHOD

CROSS REFERENCE TO RELATED APPLICATION

This application claims priority to and the benefit of Japanese Patent Application No. 2016-168351 filed on Aug. 30, 2016, the entire disclosure of which is incorporated herein by reference.

TECHNICAL FIELD

The present disclosure relates to a biological information measurement device, a biological information measurement system, and a biological information measurement method.

BACKGROUND

Biological information measurement devices that measure biological information of users, such as pulse waves, are conventionally known. Biological information is measured by various methods using biological information measurement devices. For example, a biological information measurement device measures pulse wave data by irradiating a measured part with measuring light from a light emitting element and receiving, at a light receiving element, reflected light from the measured part.

SUMMARY

A biological information measurement device according to an embodiment comprises a sensor configured to measure biological information. The sensor is supported by a wearing portion configured to be worn on a head of a human body, and is located at a position opposing at least any of an artery and a vein in the head when in a state in which the wearing portion is worn on the head.

A biological information measurement system according to an embodiment comprises a sensor configured to detect a state of blood flowing through a blood vessel, and a communication interface configured to notify an external device of the state detected. The sensor comprises a biological information measurement device and the external device. The biological information measurement device is supported by a wearing portion to be worn on a head of a human body, and located at a position opposing at least any of an artery and a vein in the head when in a state in which the wearing portion is worn on the head. The external device configured to measure biological information based on the state notified from the sensor.

A biological information measurement method by a biological information measurement device according to an embodiment comprises measuring biological information at a position opposing at least any of an artery and a vein in a head of a human body.

BRIEF DESCRIPTION OF THE DRAWINGS

In the accompanying drawings:
FIG. 4 is a table illustrating a value of signal strength measured at each of the parts illustrated in FIG. 2;
FIG. 11 is a cross-sectional view of the A-A cross section illustrated in FIG. 10 as viewed in the arrow direction;
FIG. 12 is a cross-sectional view of the A-A cross section illustrated in FIG. 10 as viewed in the arrow direction;
FIG. 13 is a cross-sectional view of the B-B cross section illustrated in FIG. 10 as viewed in the arrow direction.

DETAILED DESCRIPTION

A biological information measurement device may have difficulty in accurately measuring biological information if acquired signal strength is weak. The below-described biological information measurement device, biological information measurement system, and biological information measurement method according to the present disclosure can improve biological information measurement accuracy.

An embodiment of the present disclosure will be described in detail below, with reference to drawings.

Figure 1:
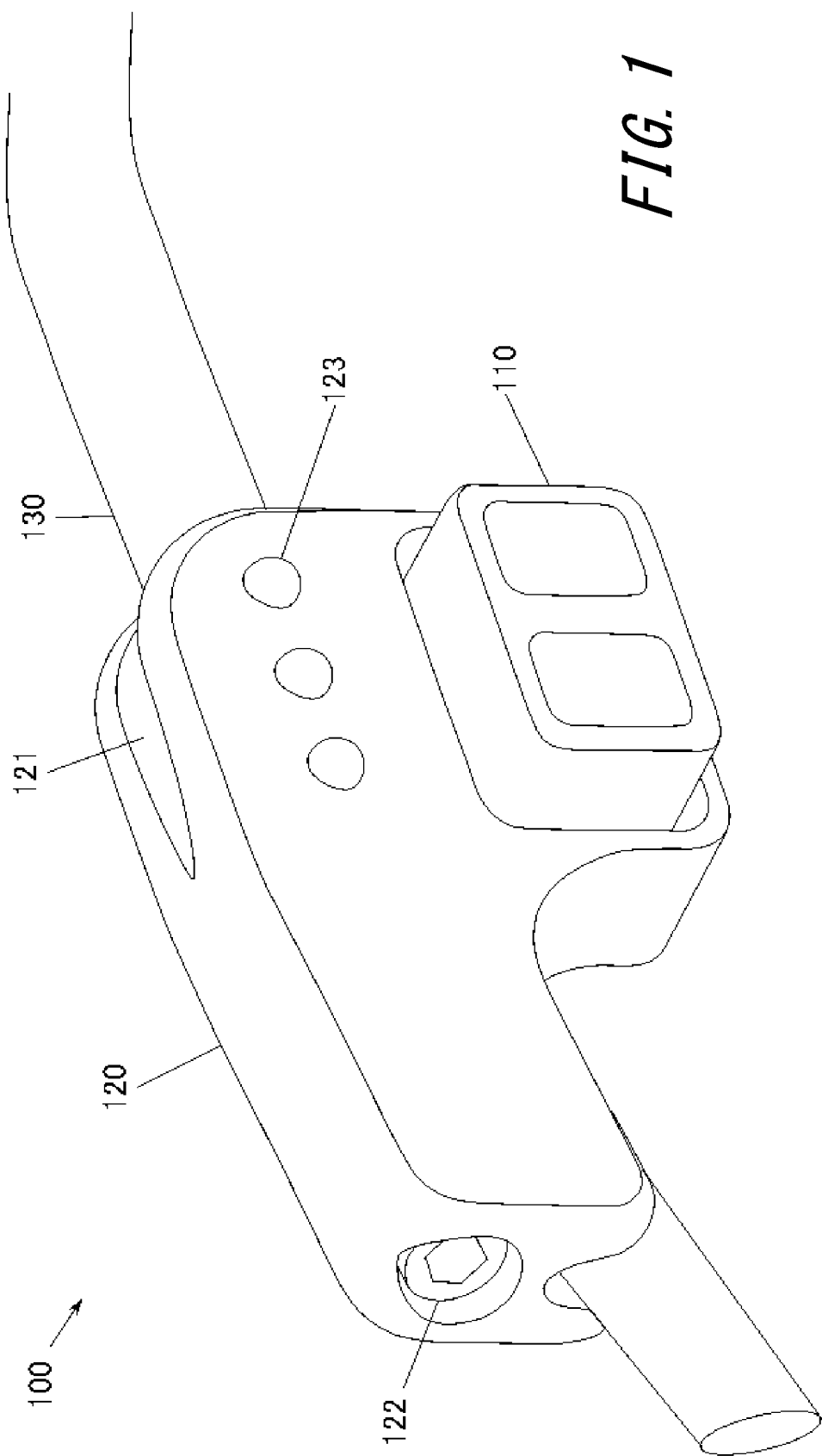
FIG. 1 is a perspective view illustrating the schematic structure of a biological information measurement device.

The schematic structure of a biological information measurement device 100 according to an embodiment of the present disclosure will be described below, with reference to FIG. 1. FIG. 1 is a perspective view illustrating the schematic structure of the biological information measurement device 100 according to an embodiment of the present disclosure.

As illustrated in FIG. 1, the biological information measurement device 100 according to an embodiment of the present disclosure includes a measurement portion 110, a fixing portion 120, and a wearing portion 130.

The measurement portion 110 measures biological information in a state in which the biological information measurement device 100 is worn on a human head. The positions subject to biological information measurement by the measurement portion 110 include positions opposing at least one of any of the arteries and veins passing through the human head. The biological information measured by the measurement portion 110 includes any biological information that can be measured by detecting the state of blood flowing through a blood vessel. Examples of the biological information measured by the measurement portion 110 include the blood flow volume of blood flowing through a blood vessel, oxygen content in hemoglobin in red blood cells, pulse wave, pulse, pulse wave velocity, blood oxygen saturation level, and blood oxygen level.

Blood vessels include arteries that carry blood away from the heart, veins that carry blood back toward the heart, and capillaries that connect the end parts (arterioles and venules) of the arteries and the veins. In an embodiment of the present disclosure, the biological information measurement target is at least any of an artery and a vein. The blood flow volume for arteries and veins is larger than for capillaries. The measurement portion 110 according to an embodiment of the present disclosure can measure biological information at a position opposing at least any of an artery and a vein more accurately than in the case of measuring biological information at a capillary.

The fixing portion 120 supports the measurement portion 110, and is fixed to the wearing portion 130. As illustrated in FIG. 1, the fixing portion 120 includes a through hole 121, a fixing implement 122, and a charging terminal 123.

The through hole 121 includes a hole for inserting the wearing portion 130 through the fixing portion 120. The fixing implement 122 includes a component for fixing the fixing portion 120 to the wearing portion 130 in a state in which the wearing portion 130 is inserted through the through hole 121. The fixing implement 122 is any implement for fixing the fixing portion 120 to the wearing portion 130 in a state in which the wearing portion 130 is inserted through the through hole 121, and includes a fixing component such as a bolt or a screw.

Thus, the fixing portion 120 is removably fixed to the wearing portion 130 by the fixing implement 122. Therefore, the measurement portion 110 can be mounted on any part of the wearing portion 130 via the fixing portion 120, and can be mounted on another wearing portion different from the wearing portion 130 illustrated in FIG. 1.

The charging terminal 123 includes a terminal for charging a secondary battery. The secondary battery supplies power for operation of the measurement portion 110.

The wearing portion 130 is worn on the human head. The wearing portion 130 includes any appliance, device, apparatus, clothing, instrument, protector, tool, or the like which is worn on the human head. Examples of the wearing portion 130 include wearable devices, neck bands, spectacles, headphones, earphones, goggles, head microphones, earphone microphones, headsets, head mounted displays, hearing aids, hats, helmets, and masks.

An embodiment of the present disclosure describes an example in which the position subject to biological information measurement by the measurement portion 110 is the head. However, the position that can be subject to biological information measurement by the measurement portion 110 may be other than the head. Since the head includes the skull, large blood vessels are typically situated near its surface. Hence, fresh blood delivered to the brain and blood containing a large amount of oxyhemoglobin flow into the head. The measurement portion 110 according to an embodiment of the present disclosure can thus measure biological information in the head accurately. In an embodiment of the present disclosure described below, the measurement portion 110 measures biological information at the "harmony crevice" or the "floating white" as an example of a part subjected to biological information measurement.

Figure 2:
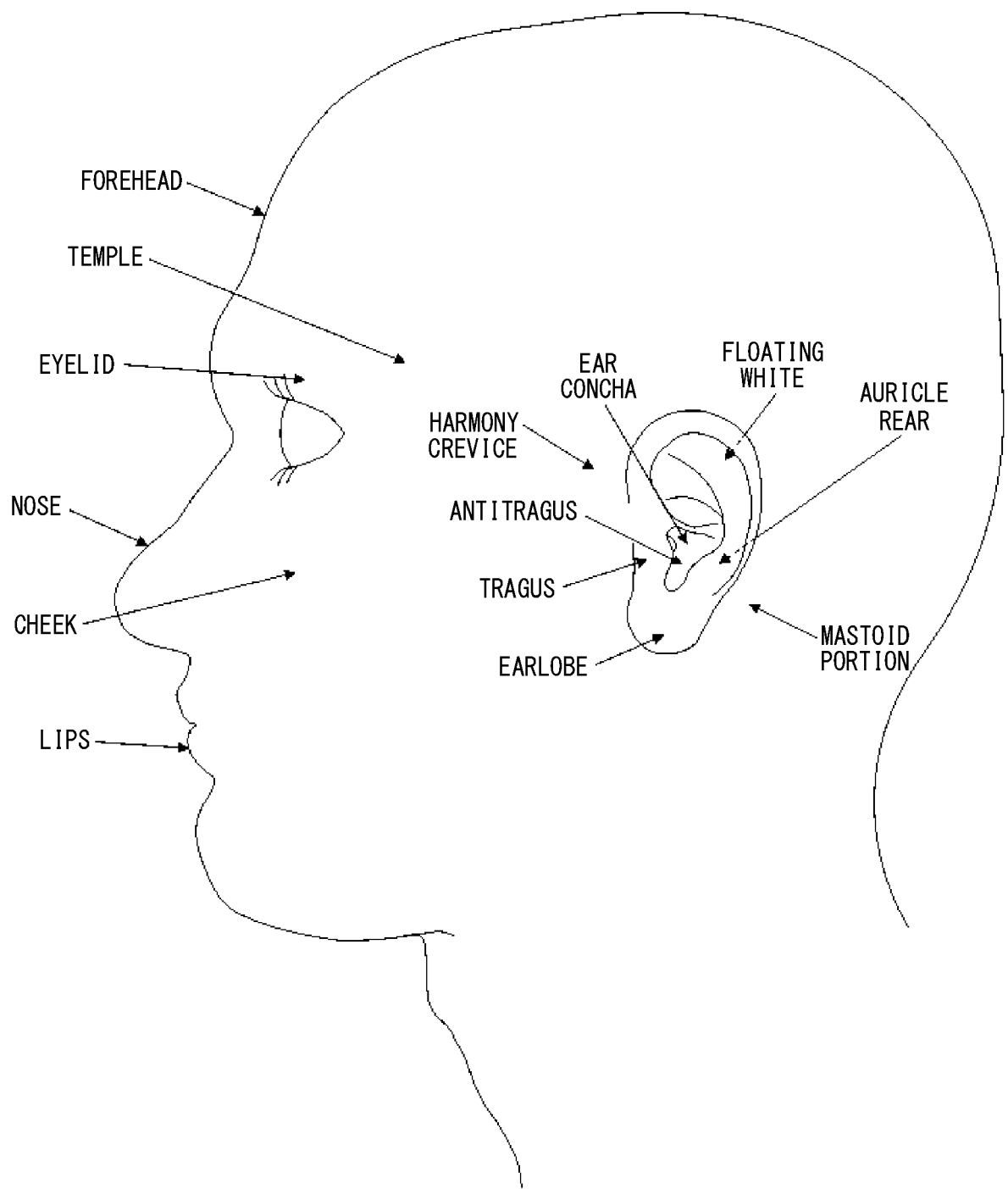
FIG. 2 is a view illustrating the position and name of each part of a human head.

FIG. 2 is a diagram illustrating the position and name of each part on the head of the human body. The "harmony crevice" is a part located in a depression of the cheekbone anterior to the root of each of the right and left ears, as illustrated in FIG. 2. Blood vessels called the superficial temporal artery and the superficial temporal vein run shallow under the skin of the "harmony crevice".

The "floating white" is a part located on the hairline behind the ear, as illustrated in FIG. 2. Blood vessels called the posterior auricular artery and the posterior auricular vein run shallow under the skin of the "floating white". These blood vessels are blood vessels from among the blood vessels in the human head which have particularly high blood flow volumes and blood flow volumes which change greatly in accordance with the heartbeat. The "blood flow volume" herein encompasses the volume of blood flowing per unit time and information indicating the volume of blood.

Thus, the measurement portion 110 can accurately measure biological information at the "harmony crevice" or the "floating white" points opposing these blood vessels. Since blood vessels with large blood flow volumes run shallow under the skin of the "harmony crevice" and the "floating white", the measurement portion 110 can accurately measure biological information even when there is a difference in physique between users who use the biological information measurement device 100 or a deviation from the position at which the measurement portion 110 is worn on the head.

The "harmony crevice" and the "floating white" are parts where hair is less likely to grow. The measurement portion 110 is therefore less affected by hair when measuring biological information, and can accurately measure biological information.

The "harmony crevice" and the "floating white" are located near the ear, as illustrated in FIG. 2. Hence, the measurement portion 110 according to an embodiment of the present disclosure can be included in any appliance, device, apparatus, clothing, instrument, protector, or tool that can be worn on the head of the human body.

Figure 3:
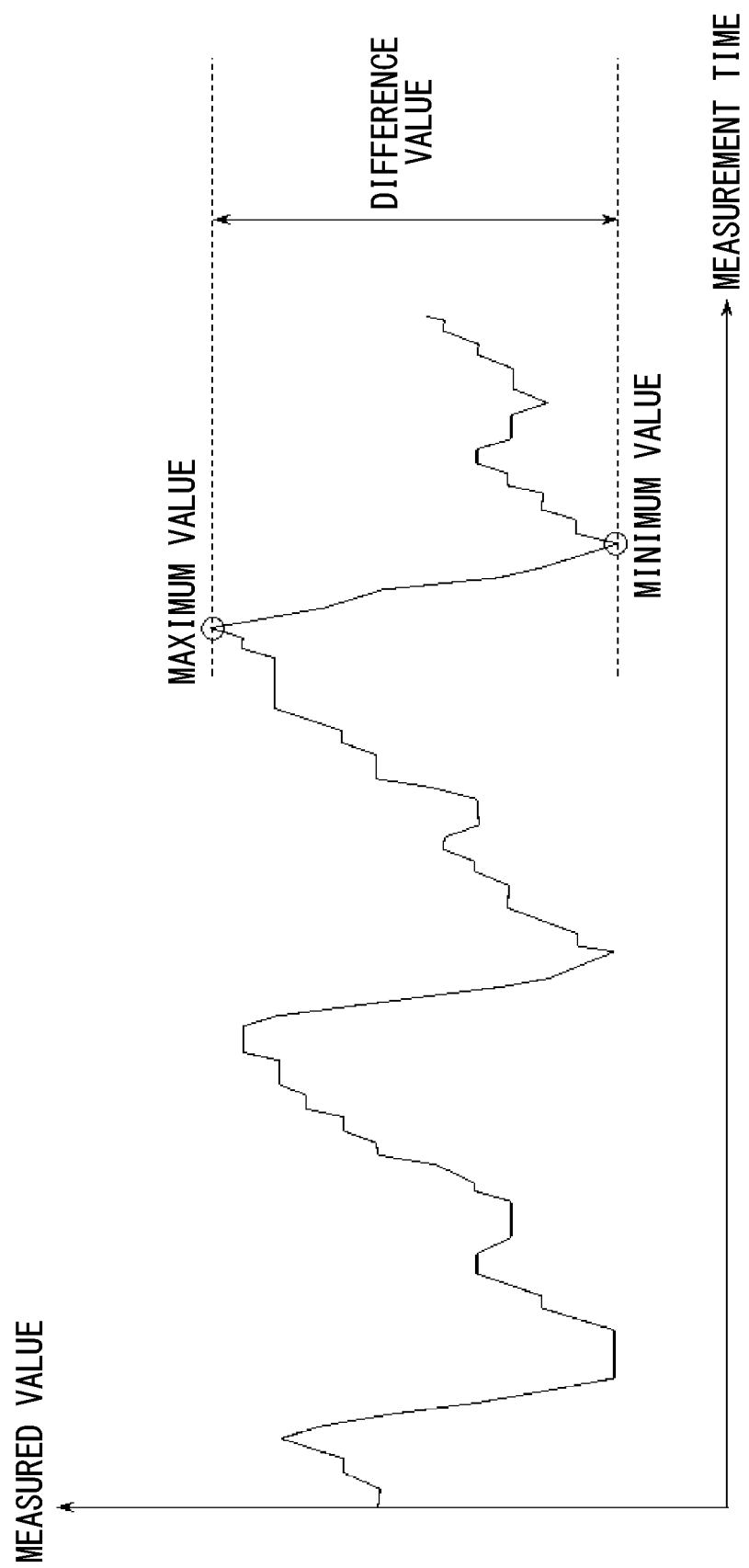
FIG. 3 is a graph illustrating the temporal changes of a measured value of signal strength.

FIG. 3 is a graph illustrating the temporal changes of the value of signal strength measured by the measurement portion 110. From the measured value, the measurement portion 110 can measure biological information such as the blood flow volume of blood flowing through a blood vessel, oxygen content in hemoglobin in red blood cells, pulse wave, pulse, pulse wave velocity, blood oxygen saturation level, or blood oxygen level. As illustrated in FIG. 3, the signal strength measured by the measurement portion 110 changes periodically with time.

FIG. 4 is a table illustrating the value of signal strength measured by the measurement portion 110 at each of the parts illustrated in FIG. 2. In FIG. 4, a greater difference between the maximum value and the minimum value of the measured value indicates higher signal strength measured by the measurement portion 110. FIG. 4 illustrates the maximum value, the minimum value, and the difference value between the maximum value and the minimum value in any one cycle of the periodic change of signal strength illustrated in FIG. 3.

As illustrated in FIG. 4, the difference values for the "harmony crevice" and the "floating white" are significantly larger than the difference values for the other parts. It can be understood from these results that the measurement portion 110 according to an embodiment of the present disclosure can accurately measure biological information at the "harmony crevice" and the "floating white".

Figure 5:
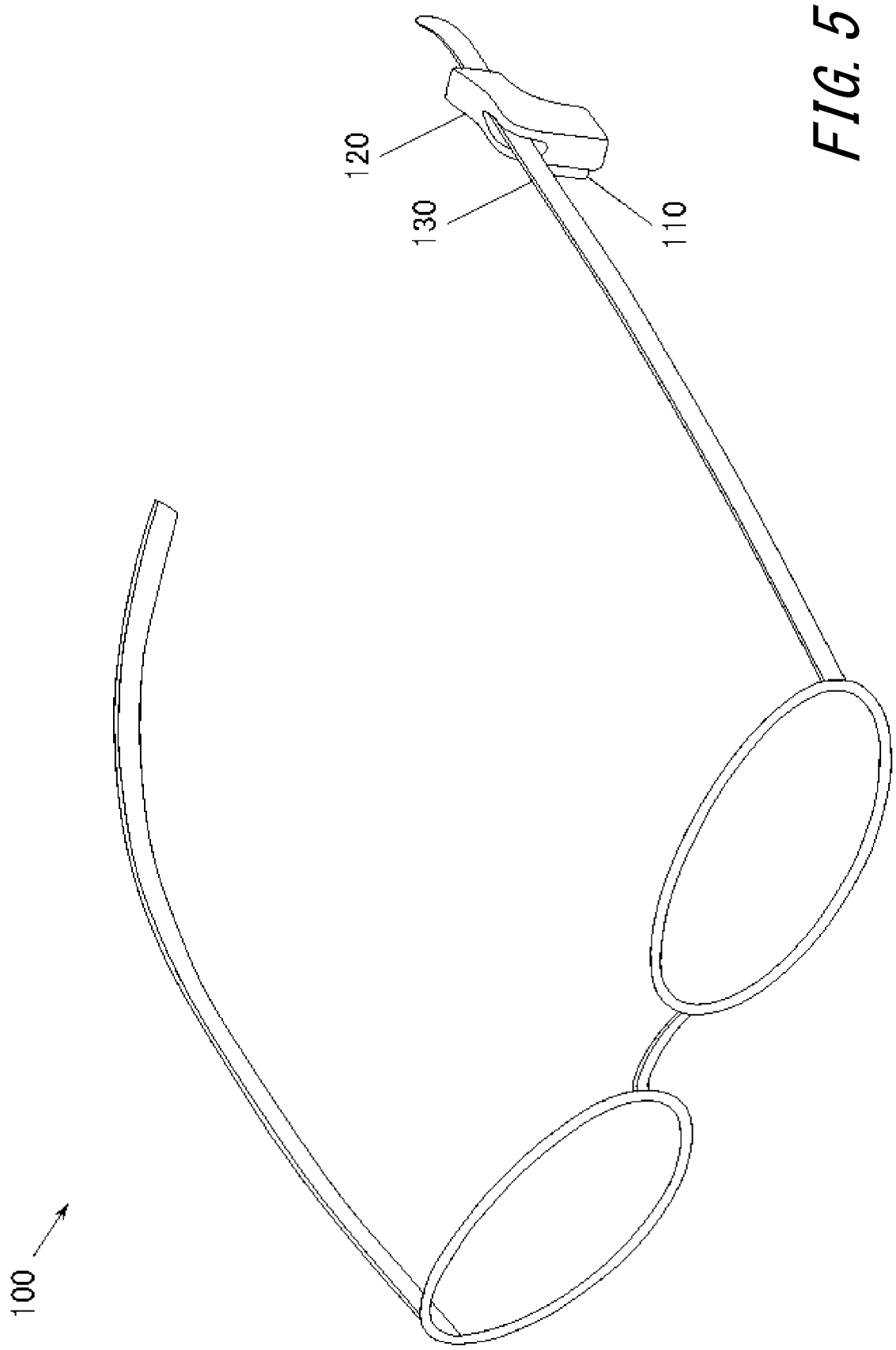
FIG. 5 is a perspective view illustrating the schematic structure of a biological information measurement device (spectacle type)

FIG. 5 is a perspective view illustrating the schematic structure of a spectacle-type biological information measurement device 100. FIG. 5 illustrates an example in which, in the case where the wearing portion 130 is a pair of spectacles, the measurement portion 110 is mounted on a part of the spectacles that fits over the ear.

Figure 6:
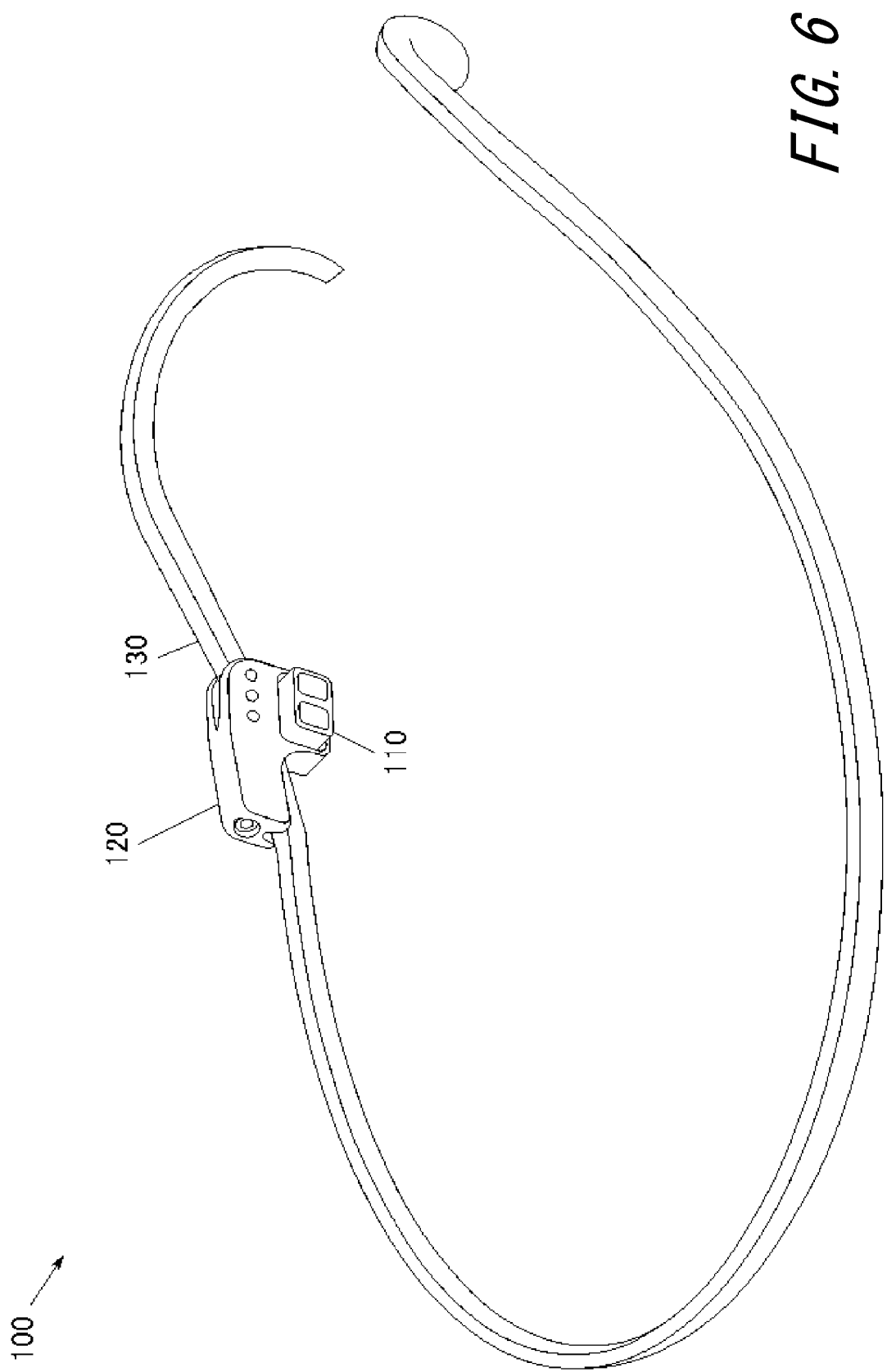
FIG. 6 is a perspective view illustrating the schematic structure of a biological information measurement device (neck band type)

FIG. 6 is a perspective view illustrating the schematic structure of a neck band-type biological information measurement device 100. FIG. 6 illustrates an example in which, in the case where the wearing portion 130 is a neck band, the measurement portion 110 is mounted on a part of the neck band that fits over the ear.

Figure 7:
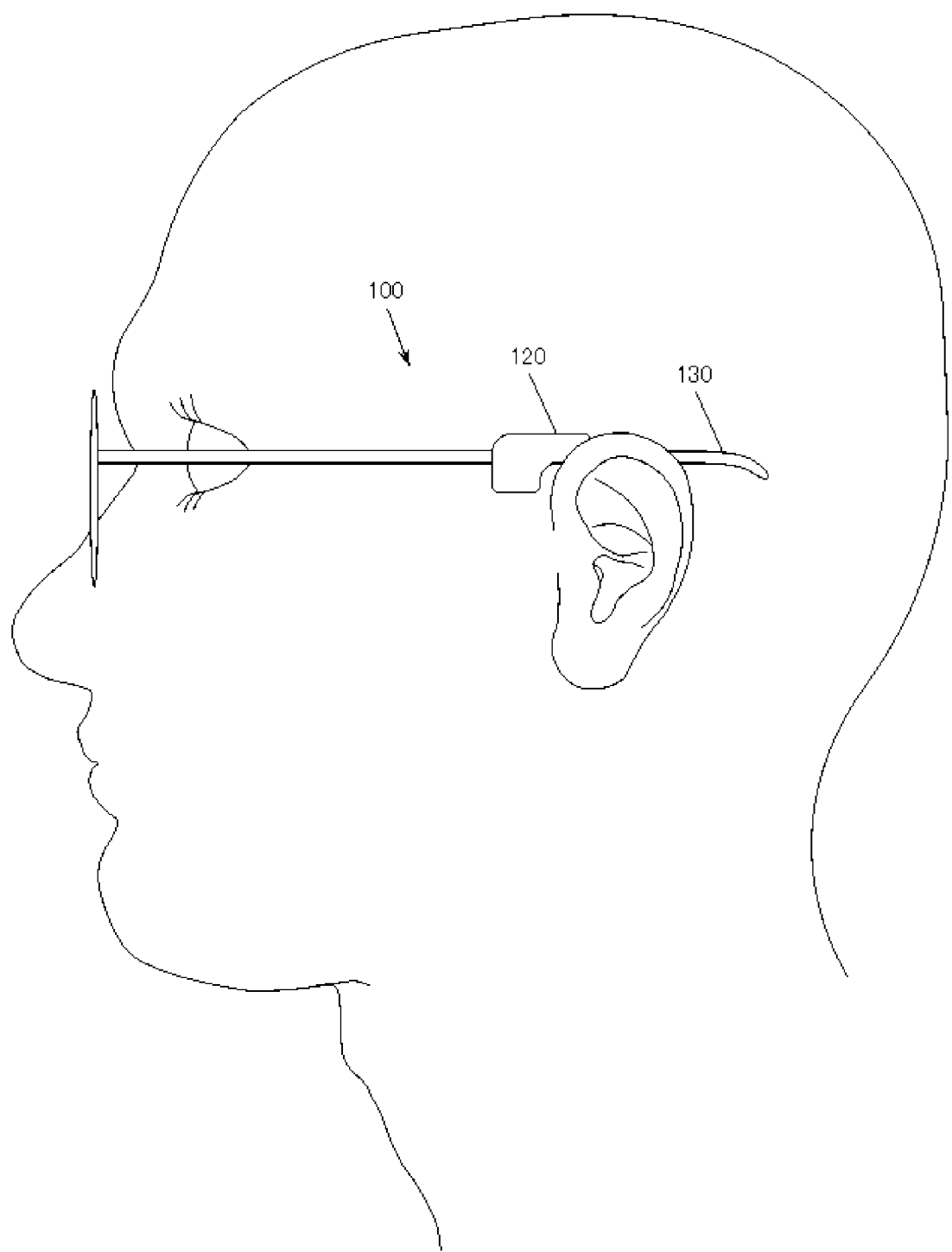
FIG. 7 is a side view illustrating a human head on which the biological information measurement device (spectacle type) is worn.

FIG. 7 is a side view illustrating a human head on which the spectacle-type biological information measurement device 100 is worn. FIG. 7 illustrates an example in which, in the case where the wearing portion 130 is a pair of spectacles, the measurement portion 110 is mounted so as to be located at the "harmony crevice".

Figure 8:
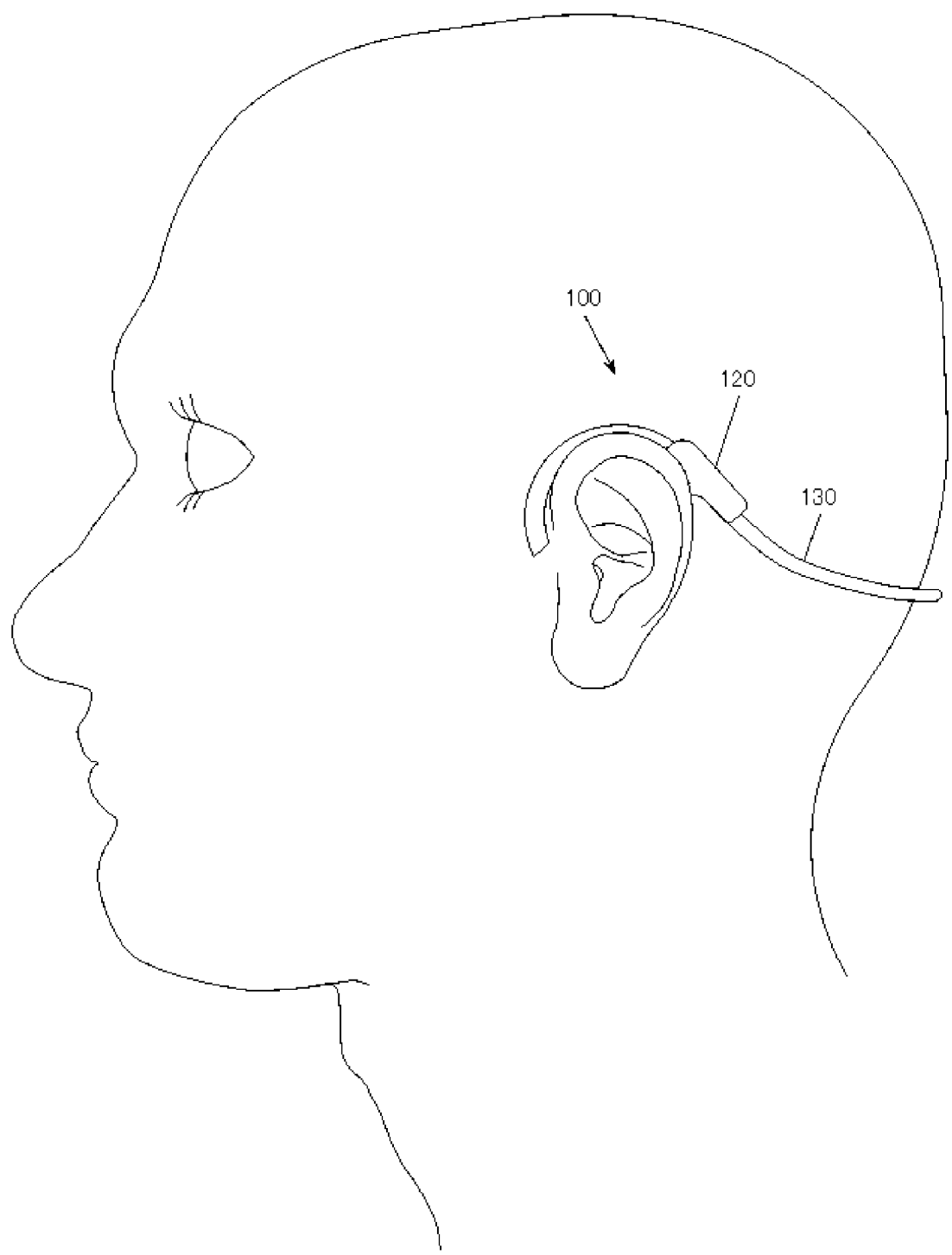
FIG. 8 is a side view illustrating a human head on which the biological information measurement device (neck band type) is worn.

FIG. 8 is a side view illustrating the head of the human body on which the neck band-type biological information measurement device 100 is worn. FIG. 8 illustrates an example in which, in the case where the wearing portion 130 is a neck band, the measurement portion 110 is mounted so as to be located at the "floating white".

Figure 9:
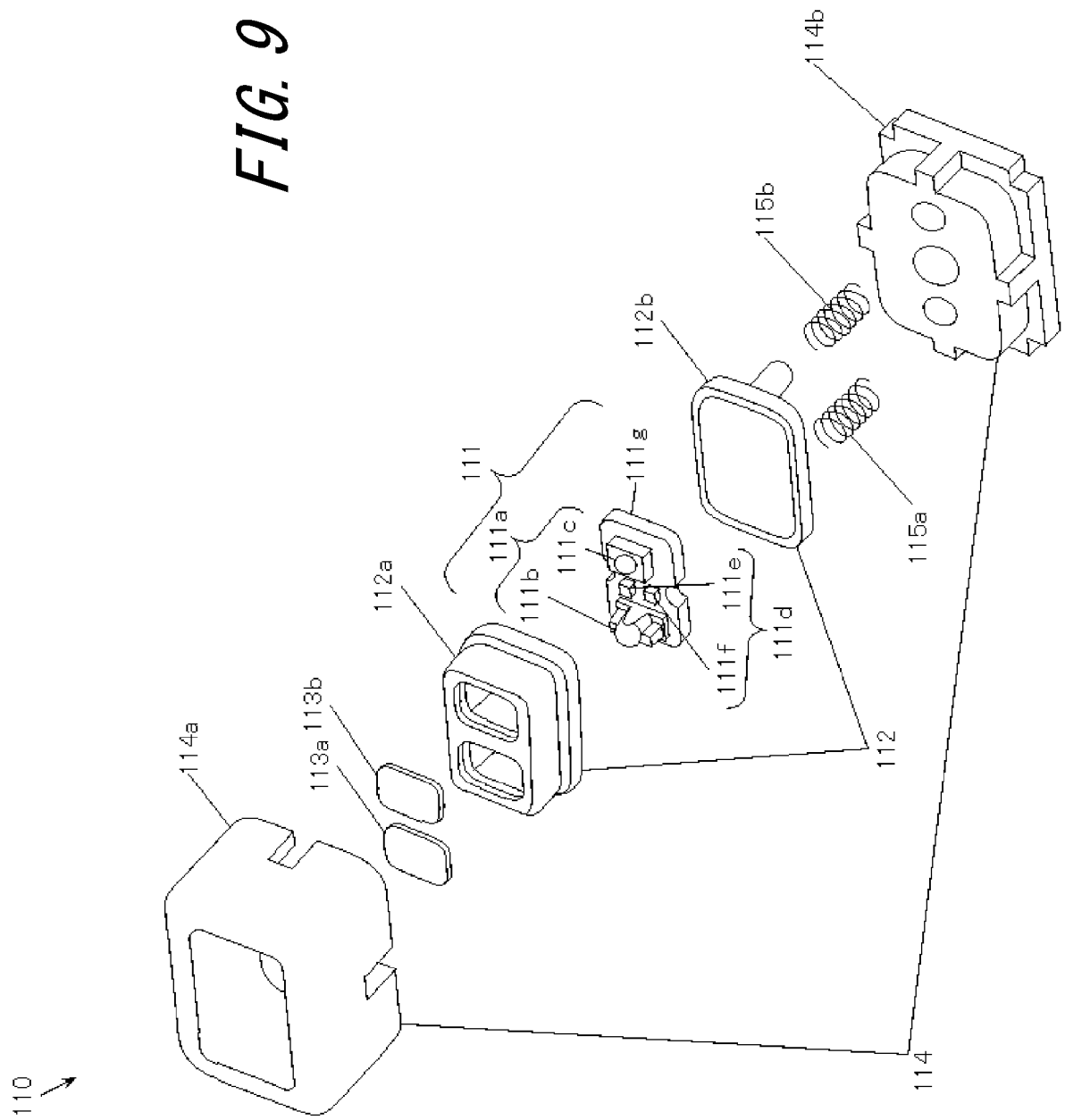
FIG. 9 is an exploded view illustrating the schematic structure of a measurement portion.
Figure 10:
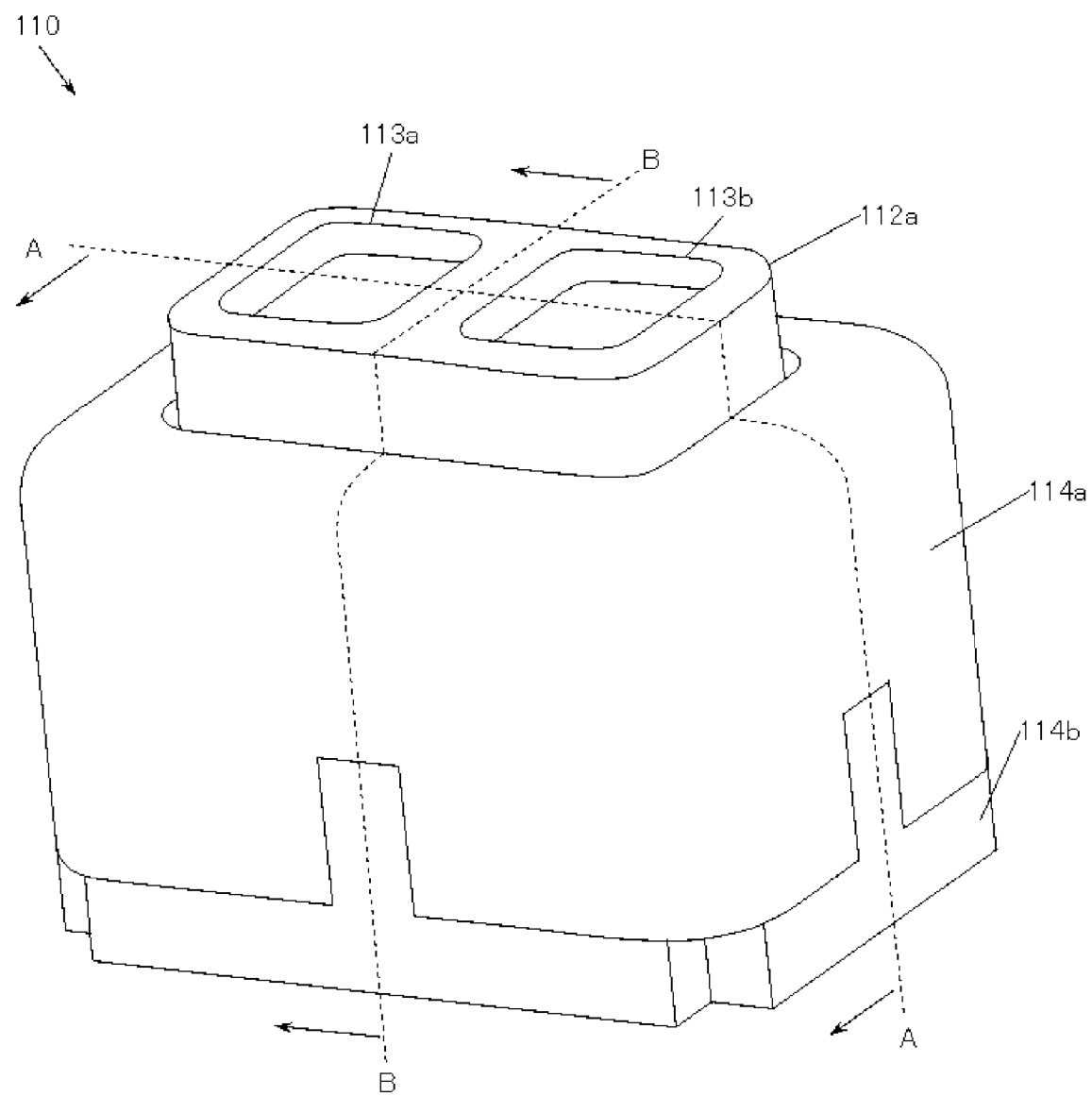
FIG. 10 is a perspective view illustrating the schematic structure of the measurement portion.

The schematic structure of the measurement portion 110 will be described below, with reference to FIGS. 9 to 13. FIG. 9 is an exploded view illustrating the schematic structure of the measurement portion 110. FIG. 10 is a perspective view illustrating the schematic structure of the measurement portion 110. FIG. 10 is a perspective view illustrating an assembly of the components illustrated in FIG. 9. FIGS. 11 and 12 are cross-sectional views illustrating the schematic structure of the A-A cross section illustrated in FIG. 10 viewed in the arrow direction. FIG. 13 is a cross-sectional view illustrating the schematic structure of the B-B cross section illustrated in FIG. 10 viewed in the arrow direction.

As illustrated in FIG. 9, the measurement portion 110 includes a sensor 111, an inner case 112, an optical emitter cover 113$a$, an optical detector cover 113$b$, an outer case 114, an elastic member 115$a$, and an elastic member 115$b$.

The sensor 111 detects the state of blood flowing through a blood vessel to measure biological information. As illustrated in FIG. 9, the sensor 111 includes a first sensor 111$a$, a second sensor 111$d$, and a circuit board 111$g$. An example of the state of blood detected by the sensor 111 is the amount of oxyhemoglobin contained in the blood. Based on the detected amount of oxyhemoglobin, the sensor 111 can measure biological information such as the blood flow volume of blood flowing through a blood vessel, oxygen content in hemoglobin in red blood cells, pulse wave, pulse, pulse wave velocity, blood oxygen saturation level, or blood oxygen level.

The first sensor 111$a$ includes an optical emitter 111$b$ and an optical detector 111$c$, and detects the state of blood flowing through the blood vessel. The optical emitter 111$b$ includes a light emitting element such as a light emitting diode (LED) or a laser diode (LD). The optical detector 111$c$ includes a light receiving element such as a phototransistor (PT) or a photodiode (PD). The optical detector 111$c$ receives reflected light of light emitted from the optical emitter 111$b$, and outputs a signal corresponding to the intensity of the received light.

Biological information obtainable by the optical emitter 111$b$ and the optical detector 111$c$ includes pulse wave. In the case of measuring the pulse wave, the sensor 111 emits light easily reflectible by blood toward the human body from the optical emitter 111$b$, and receives the light reflected from the human body by the optical detector 111$c$. The sensor 111 analyzes a signal output from the optical detector 111$c$ according to the intensity of the received light, to measure the pulse wave. In an embodiment of the present disclosure, reflection includes scattering.

The second sensor 111$d$ includes an acceleration sensor 111$e$ and a gyro sensor 111$f$, and detects movement of the wearer. The acceleration sensor 111$e$ detects acceleration of the wearer. The gyro sensor 111$f$ detects angular velocity or angular acceleration of the wearer.

The second sensor 111$d$ may include any sensor capable of detecting the movement of the wearer, besides the acceleration sensor 111$e$ and the gyro sensor 111$f$. The second sensor 111$d$ may include only one of the acceleration sensor 111$e$ and the gyro sensor 111$f$.

Because blood is a substance having a weight, when a person moves, the speed of blood flow may increase or decrease with the movement. Thus, the sensor 111 may be unable to accurately measure biological information when the wearer of the biological information measurement device 100 moves.

The sensor 111 according to an embodiment of the present disclosure detects the movement of the wearer by the second sensor 111$d$, and corrects for the influence of the movement of the wearer on the biological information based on the detected movement. Consequently, the sensor 111 can accurately measure the biological information, without being affected by the movement of the wearer. The second sensor 111$d$ may be located in the sensor 111, or located at any position at which the movement of the wearer can be detected.

The circuit board 111$g$ includes a substrate on which not only the first sensor 111$a$ and the second sensor 111$d$ but also other components, equipment, and devices constituting the sensor 111, such as a processor, a storage device, a network interface, and electronic components, are mounted and connected by wiring.

The inner case 112 includes an inner case top portion 112$a$ and an inner case bottom portion 112$b$, and covers the sensor 111 to block outside light and protect the inside of the inner case 112. Since one of the aims of the inner case 112 is to block outside light, the inner case 112 may have a high light blocking property. For example, the inner case 112 may be made of acrylonitrile butadiene styrene (ABS) resin.

The inner case top portion 112$a$ has openings in the light emitting direction of the optical emitter 111$b$ and in the light receiving direction of the optical detector 111$c$.

The optical emitter cover 113$a$ and the optical detector cover 113$b$ both allow light of the wavelength emitted by the optical emitter 111$b$ to pass through. The optical emitter cover 113$a$ and the optical detector cover 113$b$ are attached to the openings of the inner case top portion 112$a$, and protect the inside of the inner case 112.

The outer case 114 includes an outer case top portion 114$a$ and an outer case bottom portion 114$b$. The outer case 114 supports the inner case 112 in the outer case 114 via the elastic members 115$a$ and 115$b$ so that the inner case 112 is displaceable in all directions. The outer case top portion 114$a$ has an opening on the inner case top portion 112$a$ side.

The elastic members 115$a$ and 115$b$ are located to exert elastic forces between the inner case bottom portion 112$b$ and the outer case bottom portion 114$b$, and support the inner case 112 so as to be displaceable in all directions in the outer case 114. The elastic members 115$a$ and 115$b$ are any elastic members that produce elastic forces, such as springs, rubber members, flexible resin members, members using hydraulic pressure, members using pneumatic pressure, and members using water pressure.

When these components are assembled, the inner case 112 projects outward from the outer case 114 due to the elastic forces of the elastic members 115a and 115b, as illustrated in FIG. 10. Accordingly, when wearing the biological information measurement device 100 on the human head, the inner case 112 of the measurement portion 110 comes into contact with the head epidermis before the outer case 114 of the measurement portion 110.

The measurement portion 110 is supported by the fixing portion 120 and fixed to the wearing portion 130 so that, in a state in which the biological information measurement device 100 is worn on the head of the human body, the measurement portion 110 emits light toward the human body from the optical emitter 111b and receives reflected light from the human body by the optical detector 111c.

After the inner case 112 comes into contact with the head epidermis, at least one of the elastic members 115a and 115b is compressed by the pressing force from the head epidermis, as a result of which the inner case 112 withdraws into the outer case 114, as illustrated in the lower part of FIG. 11.

When the head epidermis moves relative to the measurement portion 110 with the movement of the human body, the inner case 112 moves so as to follow the head epidermis from the state illustrated in the upper part of FIG. 12 to the state illustrated in the lower part of FIG. 12 or from the state illustrated in the upper part of FIG. 13 to the state illustrated in the lower part of FIG. 13. The inner case 112 is therefore constantly in close contact with the head epidermis.

In this manner, by use of the elastic members 115a and 115b, the measurement portion 110 is supported so as to be displaceable in all directions relative to the wearing portion 130 in a state in which the fixing portion 120 is fixed to the wearing portion 130. This enables the measurement portion 110 to maintain a constant distance from the blood vessel. Hence, the measurement portion 110 can accurately measure biological information.

By use of the elastic members 115a and 115b, the inner case 112 is constantly in close contact with the head epidermis, so that the measurement portion 110 can prevent outside light from entering the inner case 112. Thus, the measurement portion 110 according to an embodiment of the present disclosure can accurately measure biological information.

By use of the elastic members 115a and 115b, the measurement portion 110 can reduce the impact caused by the contact between the inner case 112 and the head epidermis and the force of the inner case 112 pressing the head epidermis. Thus, the measurement portion 110 according to an embodiment of the present disclosure can improve the sensation of pressure on the head epidermis to improve wearing sensation.

Figure 14:
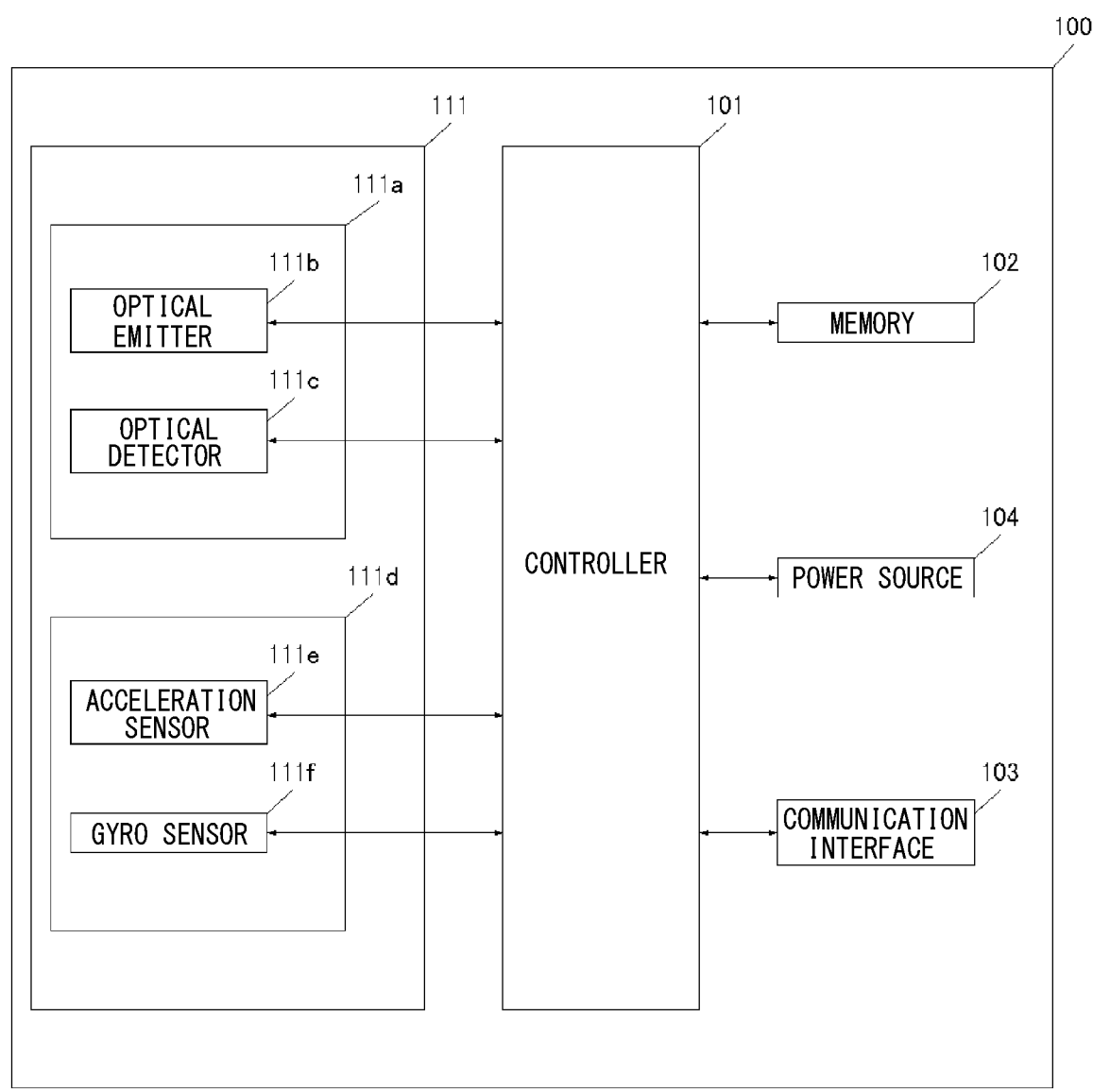
FIG. 14 is a block diagram illustrating the functional structure of the biological information measurement device.

FIG. 14 is a block diagram illustrating the functional structure of the biological information measurement device 100. As illustrated in FIG. 14, the biological information measurement device 100 includes a controller 101, a memory 102, a communication interface 103, a power source 104, and the sensor 111.

The controller 101 includes a processor that controls and manages the entire sensor 111 by, for example, controlling the light emission of the optical emitter 111b and measuring biological information based on signals output from the optical detector 111c, the acceleration sensor 111e, and the gyro sensor 111f. The controller 101 includes, for example, a processor such as a central processing unit (CPU) that executes a program defining a control procedure and a program for measuring biological information.

The memory 102 includes semiconductor memory, magnetic memory, or the like, and stores various data and various programs and also functions as working memory. The data stored in the memory 102 includes, for example, data relating to measured biological information and parameters for operating the sensor 111. The programs stored in the memory 102 include, for example, a program for operating the sensor 111 and a program for measuring biological information based on signals output from the optical detector 111c, the acceleration sensor 111e, and the gyro sensor 111f.

The communication interface 103 transmits and receives various data to and from an external device, through wired or wireless communication with the external device. For example, the communication interface 103 communicates with a device (e.g. a mobile phone, a smartphone, a tablet, or a personal computer) operated by the wearer of the biological information measurement device 100 or a server device located on a network, and transmits measurement results of biological information measured by the sensor 111 to the device.

The power source 104 includes a secondary battery such as a lithium-ion battery and a control circuit for controlling charging and discharging of the secondary battery, and supplies power to the entire sensor 111. The power source 104 may include a primary battery such as a button battery, instead of the secondary battery.

Figure 15:
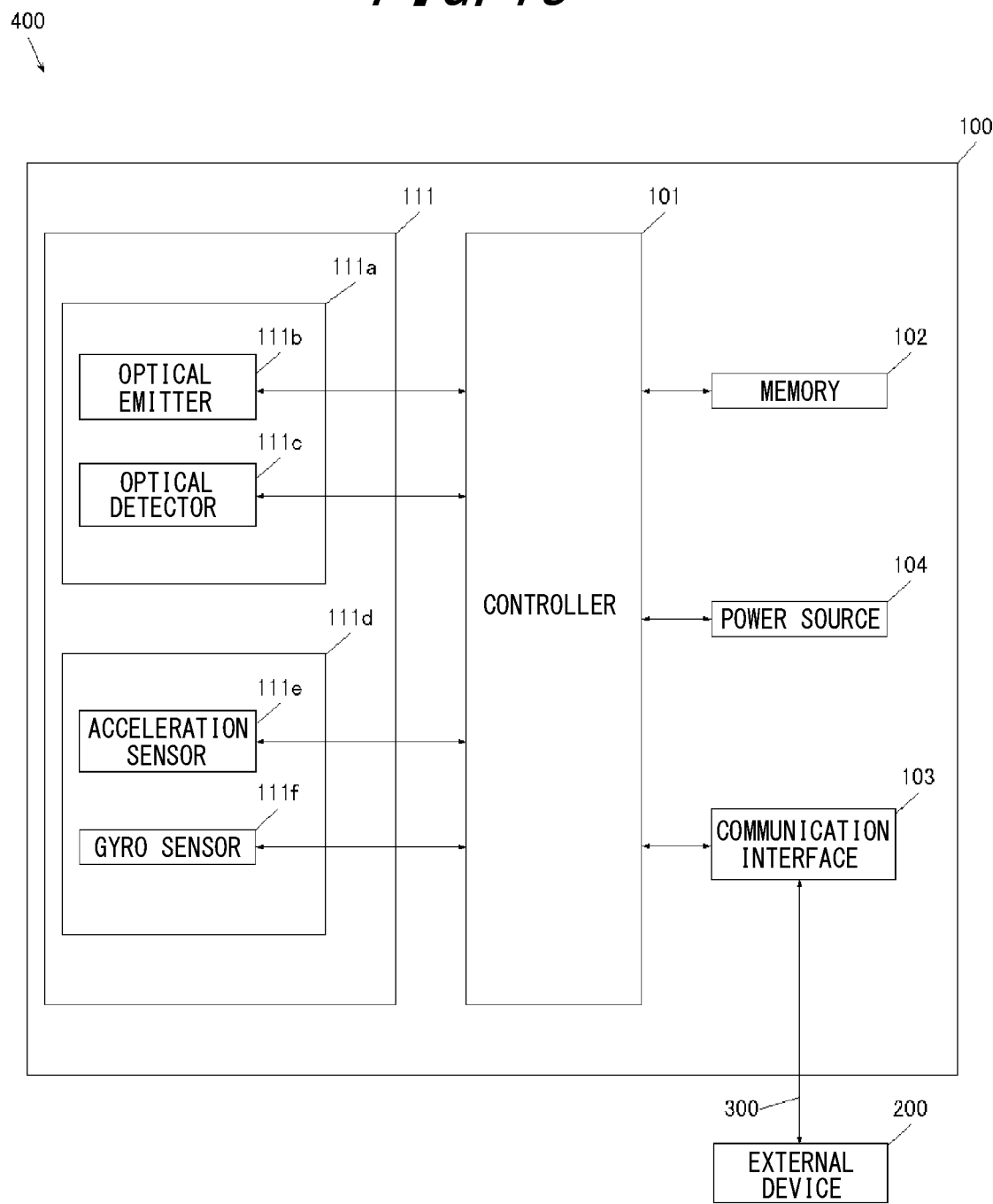
FIG. 15 is a diagram illustrating a biological information measurement system.

For example, an embodiment of the present disclosure may be a biological information measurement system 400 in which the biological information measurement device 100 and an external device 200 are connected via a network 300, as illustrated in FIG. 15.

In the biological information measurement system 400, the biological information measurement device 100 may be configured as a detection device that notifies the detection results by the first sensor 111a and the second sensor 111d to the external device 200, without performing biological information measurement. In the case where the biological information measurement device 100 is configured as such a detection device, the external device 200 may be configured to measure biological information based on the detection results notified from the biological information measurement device 100. Examples of the external device 200 include mobile phones, smartphones, tablets, personal computers, and server devices.

The present disclosure is not limited to the foregoing embodiments, and various modifications and changes are possible. For example, the functions included in the components, etc. may be rearranged without logical inconsistency, and a plurality of components, etc. may be combined into one component, etc. and a component, etc. may be divided into a plurality of components, etc.

For example, although the foregoing embodiments describe examples in which biological information obtainable by the optical emitter 111b and the optical detector 111c is pulse wave, the present disclosure is not limited to this. Biological information obtainable by the optical emitter 111b and the optical detector 111c may include, for example, blood oxygen saturation level or blood oxygen level.

To measure the blood oxygen saturation level or the blood oxygen level, the sensor 111 emits, from the optical emitter 111b toward the human body, light of a wavelength that differs in absorbance depending on the oxygen content in hemoglobin in red blood cells, and receives reflected light from the human body by the optical detector 111c. The sensor 111 analyzes a signal output from the optical detector 111c according to the intensity of the received light, to measure the blood oxygen saturation level or the blood oxygen level.

Although the foregoing embodiments describe examples in which the sensor 111 has a pulse wave measurement function, the present disclosure is not limited to this. Since the sensor 111 can obtain pulse wave with high accuracy, for example, the sensor 111 may have a function of measuring any biological information measurable based on the pulse wave. For example, the sensor 111 may have a function of measuring blood pressure, pulse, or pulse wave velocity from the obtained pulse wave.

Although the foregoing embodiments describe examples in which the biological information measurement device 100 has a function of measuring biological information by the optical emitter 111b and the optical detector 111c, the present disclosure is not limited to this. The biological information measurement device 100 may have a function of measuring biological information by any method with which biological information can be measured, such as a method using a sound wave or a radio wave.

The invention claimed is:

1. A biological information measurement device comprising
    a sensor configured to measure biological information and configured to detect movement of a wearer of the biological information measurement device;
    an inner case to cover the sensor; and
    an outer case to support the inner case via elastic members, the elastic members being positioned to exert elastic forces between the inner case and the outer case,
    wherein the sensor is supported by a wearing portion configured to be worn on a head of a human body, and is located at a position opposing at least any of an artery and a vein in the head when in a state in which the wearing portion is worn on the head,
    the sensor is configured to correct for influence of the detected movement on the measured biological information based on the detected movement, and
    the biological information includes at least any of a blood flow volume of blood flowing through a blood vessel, an oxygen content in hemoglobin in red blood cells, a pulse wave, a pulse, a pulse wave velocity, a blood oxygen saturation level, and a blood oxygen level.

2. The biological information measurement device according to claim 1, wherein the artery includes at least any of a superficial temporal artery and a posterior auricular artery.

3. The biological information measurement device according to claim 1, wherein the vein includes at least any of a superficial temporal vein and a posterior auricular vein.

4. The biological information measurement device according to claim 1, wherein the sensor is supported by the wearing portion at a position opposing at least any of a harmony crevice and a floating white of the human body when in the state in which the wearing portion is worn on the head.

5. The biological information measurement device according to claim 1, wherein the sensor is displaceably supported relative to the wearing portion.

6. The biological information measurement device according to claim 1, comprising the wearing portion.

7. The biological information measurement device according to claim 1, wherein the wearing portion is any of a wearable device, a neck band, spectacles, headphones, earphones, goggles, head microphones, earphone microphones, a headset, a head mounted display, a hearing aid, a hat, a helmet, and a mask to be worn on the head of the human body.

8. The biological information measurement device according to claim 1, wherein the sensor includes:
    an optical emitter; and
    an optical detector configured to receive, from the at least any of the artery and the vein, reflected light of light emitted from the optical emitter, and output a signal corresponding to an intensity of the reflected light received, and
    the sensor is configured to measure the biological information based on the signal output.

9. The biological information measurement device according to claim 8, wherein the elastic members are disposed at a side opposed to a light emitting part of the optical emitter, in a direction parallel to a direction from the optical emitter to the optical detector, to apply pressure towards the inner case including the optical emitter and the optical detector.

10. The biological information measurement device according to claim 1, wherein the sensor is removably attachable to the wearing portion.

11. The biological information measurement device according to claim 1, comprising:
    a power source configured to supply power for operation of the sensor; and
    a charging terminal configured to charge the power source.

12. The biological information measurement device according to claim 1, wherein the inner case is configured to project outward from the outer case due to the elastic forces exerted by the elastic members.

13. The biological information measurement device according to claim 1, wherein the inner case is configured to withdraw into the outer case, and when the inner case contacts the head, at least one of the elastic members is compressed by a pressing force from the head and the inner case withdraws into the outer case.

14. A biological information measurement system comprising:
    a biological information measurement device including: a sensor configured to detect a state of blood flowing through a blood vessel and configured to detect movement of a wearer of the biological information measurement device; an inner case to cover the sensor; an outer case to support the inner case via elastic members, the elastic members being positioned to exert elastic forces between the inner case and the outer case; and a communication interface configured to notify an external device of the state and movement detected, the sensor being supported by a wearing portion to be worn on a head of a human body, and located at a position opposing at least any of an artery and a vein in the head when in a state in which the wearing portion is worn on the head; and
    the external device configured to measure biological information based on the state notified from the sensor and configured to correct for influence of the detected movement on the measured biological information based on the detected movement,
    wherein the biological information includes at least any of a blood flow volume of blood flowing through a blood vessel, an oxygen content in hemoglobin in red blood cells, a pulse wave, a pulse, a pulse wave velocity, a blood oxygen saturation level, and a blood oxygen level.

\* \* \* \* \*